United States Patent [19]

Krauthamer

[11] Patent Number: 5,239,998
[45] Date of Patent: Aug. 31, 1993

[54] APPARATUS AND METHOD FOR FLUORESCENT EXCITATION AND DETECTION FROM POTENTIOMETRIC DYES WITH A SINGLE-ENDED OPTICAL FIBER

[75] Inventor: Victor Krauthamer, Wheaton, Md.

[73] Assignee: The United States of America as represented by the Department of Health and Human Services, Washington, D.C.

[21] Appl. No.: 732,021

[22] Filed: Jul. 18, 1991

[51] Int. Cl.⁵ ............................................. A61B 5/00
[52] U.S. Cl. .................................. 128/633; 128/634; 128/665
[58] Field of Search ............................. 128/633–634, 128/664–665; 356/36, 402

[56] References Cited

U.S. PATENT DOCUMENTS 5,101,814  4/1992  Palti ..................................... 128/635

OTHER PUBLICATIONS

Dillon et al, "Use of Voltage Sensitive Dyes to Investigate Electrical Defibrillation", *Proc. IEEE-BME*, 10, pp. 215–216.

Kudo et al, "A New Device for Monitoring Concentrations of Intracellular $Ca^{2+}$ in CNS Preparations and Its Application to the Frog's Spinal Cord", *Journal of Neuroscience Methods*, vol. 30(1989), pp. 161–168.

Grinvald et al, "Improved Fluorescent Probes for the Measurement of Rapid Changes in Membrane Potential", *Biophys. J.*, vol. 39 (1982), pp. 301–308.

Grinvald et al, "Optical Recording to Synaptic Potentials from Processes of Single Seurons Using Intracellular Potentiometric Dyes", *Biophys. J.*, vol. 51 (1987), pp. 643–651.

*Primary Examiner*—Lee S. Cohen
*Assistant Examiner*—Kevin Pontius
*Attorney, Agent, or Firm*—Lowe, Price LeBlanc & Becker

[57] ABSTRACT

A method of detecting and recording action-potential-related fluorescent changes from a remote tissue situs which has been treated with a voltage-sensitivity dye. The method utilizes a single optical fiber to both direct excitation light to the remote tissue situs and receive emitted fluorescence from the remote tissue situs. The emitted fluorescence from the remote tissue situs is directed to a photomultiplier or photodiode which produces a resulting fluorescence-related signal which is analyzed. The method and related apparatus eliminates signal noise and allows accurate recording and analysis of action-potential-related fluorescent changes.

20 Claims, 1 Drawing Sheet

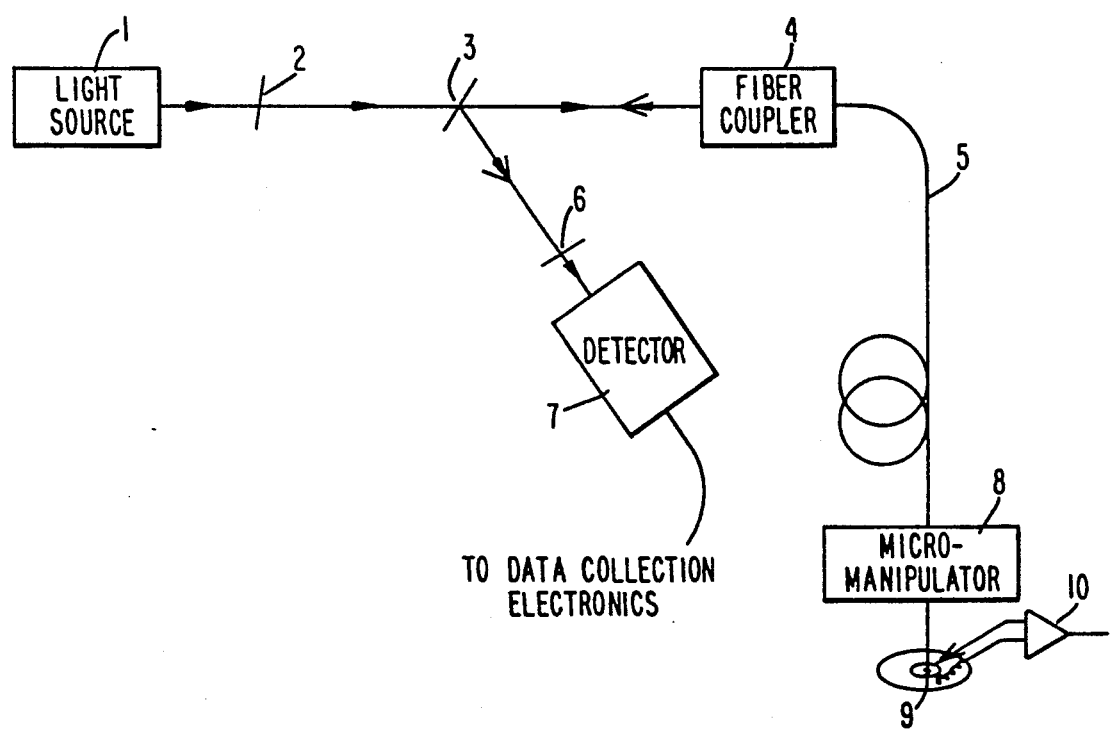

APPARATUS AND METHOD FOR FLUORESCENT EXCITATION AND DETECTION FROM POTENTIOMETRIC DYES WITH A SINGLE-ENDED OPTICAL FIBER

TECHNICAL FIELD

The present invention relates to detecting the electrical activity of cells. More particularly, the present invention relates to methods and apparatus for optically detecting action-potential-related fluorescent changes from excitable tissues stained with a voltage-sensitive dye.

BACKGROUND ART

Optical recording has, for some time, been a means of detecting the electrical activity of cells. Most optical recording techniques require the use of voltage-sensitive dyes which bind to cell membranes and respond linearly to changes in transmembrane potential by changing either in absorption or fluorescent emission.

The standard method for optically recording electrical activity of tissues stained with voltage-sensitive dyes involves the use of microscope optics. This method which relies upon microscope optics is limited because it requires a clear line-of-sight path between the required light source, the tissue under investigation, and the light detector. To provide this necessary clear line-of-sight path, extensive dissection of the tissue is often required. Accordingly, such prior art methods cannot be used in vivo.

More recent work with optical fibers has made in vivo optical recording possible. Dillon (Dillon, S. M. and Wit, A., "Use of Voltage Sensitive Dyes to Investigate Electrical Defibrillation", *Proc. IEEE-BME*, 10:2-15–216) was the first to perform in vivo optical recording in a fluorescent system in which excitation light was emitted from one fiber and fluorescence was detected from a concentric bundle of fibers.

Kudo (Kudo et al, "A New Device for Monitoring the Concentration of Intracellular $Ca^{2+}$ in CNS Preparations and its Application to the Frog Spinal Cord", *J. Neurosci. Meth.*, 30:161–168) used two fibers held in a micropipette for exciting and detecting fluorescence from a calcium-sensitive dye.

These prior art multiple fiber techniques are necessarily limited for in vivo use because the fiber bundles are large, e.g., on the order of one to several millimeters in diameter, and because the fibers must be separated to detect fluorescence.

The present invention overcomes the problems associated with prior art systems for optically detecting action-potential-related fluorescence changes from excitable tissue stained with a voltage-sensitive dye.

DISCLOSURE OF THE INVENTION

It is one object of the present invention to provide an apparatus for detecting action-potential-related fluorescent changes from excitable tissue stained with a voltage-sensitive dye.

Another object of the present invention is to provide an apparatus which utilizes a single optical fiber to deliver excitation light to and receive fluorescent emission from a remote situs.

A further object of the present invention is to provide an apparatus for detecting reaction-potential-related fluorescent changes from excitable tissue stained with a voltage-sensitive dye which has a low signal noise level.

A further object of the present invention is to provide an in vivo method of detecting electrical activity of excitable tissue.

A still further object of the present invention is to provide an in vivo method of detecting reaction-potential-related fluorescent changes from excitable tissue stained with a voltage-sensitive dye which has a low signal noise level.

According to these and further objects of the present invention which will become apparent as the description thereof proceeds, there is provided a method of detecting electrical characteristics of a remote sample situs which involves:

treating the remote sample situs with a voltage-sensitive dye;

delivering light of a sufficient wavelength to cause fluorescent emission of the dye-treated remote sample to the dye-treated remote sample by means of a single optical fiber; and receiving fluorescent emission from the dye-treated remote situs by the single optical fiber and delivering the received fluorescent emission to a detector which analyzes the received fluorescent emission.

Also provided by the present invention is an apparatus for detecting electrical characteristics of a remote sample situs which includes:

a light source for generating excitation light having a wavelength of between about 490 to 550 nm;

means to pass the excitation light through a single optical fiber to a remote sample situs;

means interposed between the light source and the single optical fiber for attenuating the excitation light;

means interposed between the attenuating means and the single optical fiber for removing light of an interfering wavelength from the excitation light;

means for directing emitted light from the remote sample to a fluorescent detector; and means positioned between the directing means and the fluorescent detector for removing light of an excitation wavelength from the emitted light.

BRIEF DESCRIPTION OF DRAWINGS

The present invention will be described with reference to the sole Figure which is given be way of a non-limiting example only in which the optical system of the present invention is schematically depicted.

BEST MODE FOR CARRYING OUT THE INVENTION

The present invention is directed to a method and apparatus for detecting fluorescence emitted at a remote situs. In particular, the present invention utilizes a single optical fiber for both directing light of an excitation wavelength to a remote situs and for receiving resulting fluorescence emitted at the remote situs.

The present invention is particularly useful in detecting and recording action-potential-related fluorescent changes from excitable tissue stained with a voltage-sensitive dye. In this regard, the present invention was specifically developed to eliminate signal noise which heretofore limited in vivo optical recording of electrical cell activity.

The optical detecting and recording apparatus according to the present invention includes a light source coupled to an optical fiber through a dichroic beam splitter, and a photodetector or photodiode. In operation, a beam of excitation light is directed through the optical fiber to a remote situs, e.g, tissue situs, to cause the remote situs to undergo a change in fluorescent characteristics, e.g., emit fluorescence. Resulting fluorescence from the remote situs returns through the optical fiber and is directed by the beam splitter to the photodetector tube which processes the resulting fluorescence-related signal in a known manner.

The present invention is particularly suitable for detecting action-potential-related fluorescent changes from excitable tissue stained with a voltage-sensitive dye. In order to significantly reduce signal noise, the present invention preferable utilizes a voltage-sensitive dye which is excitable by light of one wavelength, e.g., green, and, in response thereto, emits light of a substantially different wavelength, e.g., red. Preferred voltage-sensitive dyes found to be particularly useful for purposes of the present invention include styryl voltage-sensitive dyes, which are excited by green light, i.e., at a wavelength of about 490-550 nm and, in response thereto, emit red fluorescence, i.e., at a wavelength of about 650-700 nm.

The signal is gained by attenuating the excitation light beam by initially passing the excitation light beam through a neutral density filter to limit photodynamic damage to the tissue, and subsequently passing the attenuated excitation beam through a short-pass interference filter having a specific cutoff wavelength, e.g., about 575 nm in order to remove light having a wavelength appreciably greater than the desired excitation wavelength. Finally, resulting fluorescent emission which is returned through the optical fiber is passed though a long-pass filter which removes any light of the excitation wavelength before the returning fluorescence is received by the photomultiplier tube or photodiode.

Although the apparatus of the present invention may be utilized in conjunction with a variety of types of remote situs, the apparatus and method are particularly useful for in vivo detecting of action-potential-related fluorescent changes which occur in remote tissue situs.

The apparatus of the present invention is schematically shown in the sole Figure. As depicted, the apparatus includes a light source 1 which provides light of a suitable wavelength to excite fluorescent emission from a dye-stained tissue situs. The light source is required to produce a beam of excitation light and accordingly is preferably a laser; however, any suitable light/optic system capable of producing a beam of excitation light may be used. When utilizing styryl voltage-sensitive dyes to stain the tissue situs, the light source 1 was selected to produce green light having a wavelength of about 543 nm. In a preferred embodiment according to the present invention, a 0.5 mW HeNe laser (model LGK-7770 laser, model LGN-7460 power supply, Siemens, Iselin, N.J.) was used.

The light source 1 is coupled to an optical fiber 5 through a neutral density filter 2 and dichroic beam splitter 3. The neutral density filter 2 is positioned in the beam path of the light source 1 at a small angle thereto so that a beam of light produced from the light source 1 is not reflected directly back to the light source 1. The neutral density filter 2 is provided to attenuate the output of the light source 1 and thereby assists in reducing light-induced tissue damage.

After being attenuated by the neutral density filter 2, the beam of light from light source 1 passes through a dichroic beam splitter 3 which, like the neutral density filter 2, is slightly angled with respect to the light beam so as to permit reflected fluorescent light from being reflected into the photodetector 7. directly back toward the neutral density filter 2 and light source 1. The dichroic beam splitter 3 includes a short-pass interference filter with a cutoff wavelength which is sufficient to remove light of an interfering wavelength which contributes to unacceptable noise in the detected signals. In a preferred embodiment, utilizing the HeNe laser discussed above, the beam splitter 3 was a short-pass interference filter having a cutoff wavelength of 575 nm (model 58881, Oriel, Stratford, Conn.) and had an angle of incidence of 34 degrees, with the mirrored surface thereof facing the photomultiplier tube 7 or photodiode, discussed below.

After passing through the neutral density filter 2 and the beam splitter 3, the beam of excitation light is focussed onto a straight-cleaved optical fiber 5 by means of fiber coupler 4 in a known manner. In a preferred embodiment according to the present invention, the fiber coupler 4 (model F-1015, Newport, Fountain Valley, Calif.) included a X40, 0.4 numerical aperture microscope objective lens (model M-20X, Newport) which focussed the excitation beam into the optical fiber 5. In the preferred embodiment, the optical fiber 5 was held by a fiber chuck (model FPH-DJ, Newport).

The optical fiber 5 is chosen to have a minimum overall diameter and preferably includes a 50-100 μm core with an outer cladding to make a total diameter of up to about 140 μm. Preferred optical fibers include either a 50 μm core (type MSD, Newport), a 100 μm core (type MLD, Newport) or a 100 μm core medical fiber with a larger numerical aperture (type HCN-H0125T-14, Ensign-Bickford, Avon, Conn.), or equivalent fibers. The length of the optical fiber 5 is selected to be sufficiently long so that the distal end can easily reach a desired tissue situs, e.g, about 2 meters.

As noted above, the present invention involves excitation of a remote situs which responds thereto by a change in fluorescent characteristics. In a preferred embodiment described herebelow for illustrative purposes, the remote situs includes a voltage-sensitive-dye-stained tissue.

As a result of excitation, the voltage-sensitive dye-stained tissue emits fluorescence which passes back through optical fiber 5. The returning fluorescence is reflected off of the beam splitter 3 and passes through long-pass filter 6 which removes any excitation light. In a preferred embodiment the long-pass filter (model OG570, Schott) removed green excitation light while the excited voltage-sensitive-dye-stained tissue emitted red fluorescent light.

The emitted florescence is directed from the beam splitter 3 through the long-pass filter 6 and onto a conventional photomultiplier tube or photodiode. In a preferred embodiment, the photomultiplier tube (model R-1333 tube, model 2380 socket assembly, Hamamatsu, Bridgewater, N.J.) was powered at −1.5 KV by a D.C. power supply (model 215, Hamamatsu). In this embodiment, the output from the photomultiplier tube was terminated with a 10 KΩ resister as suggested by the instruction supplied by the manufacture.

The fluorescence-related signal produced from the photomultiplier tube is amplified, displayed and recorded with standard data acquisition techniques and equipment.

In tests, the voltage-sensitive dyes including RH237 or RH461 (Molecular Probes, Eugene, Oreg.) were applied to tissue samples utilizing the techniques described by Grinvald et al (Grinvald et al, "Improved Fluorescent Probes for the Measurement of Rapid Changes in Membrane Potential", *Biophys. J.*, 39:301–308; and Grinvald et al, "Optical recording of Synaptic Potentials from Processes of Single Neurons using Intracellular Potentiometric Dyes", *Biophys. J.*, 51:643–651), the disclosures there being expressly incorporated herein by reference.

In in vitro tests, a micromanipulator 8 was used to position the distal end of the optical fiber 5 adjacent a tissue sample a being tested while a microelectrode amplifier 10 was used to monitor electrical characteristics tissue.

In in vivo procedures, the distal end of the optical fiber 5 was positioned adjacent the tissue situs utilizing conventional techniques.

Although the invention has been described with reference to particular means, materials and embodiments, from the foregoing description, one skilled in the art can easily ascertain the essential characteristics of the present invention and various changes and modification may be made to adapt the various uses and conditions without departing from the spirit and scope of the present invention as described in the claims which follow.

What is claimed is

1. A method of detecting electrical characteristics of a remote sample situs which comprises:
   treating the remote sample situs with a voltage-sensitive dye providing a single optical fiber and a detector;
   delivering light of a sufficient wavelength to cause fluorescent emission of said dye-treated remote sample situs to said dye-treated remote sample situs by means of said single optical fiber; and
   receiving fluorescent emission from said dye-treated remote sample situs by said single optical fiber and delivering said received fluorescent emission to said detector for analyzing said received fluorescent emission.

2. A method of detecting electrical characteristics of a remote sample situs according to claim 1, wherein said remote sample situs comprises a tissue sample.

3. A method of detecting electrical characteristics of a remote sample situs according to claim 2, wherein said tissue sample is within a subject's body.

4. A method of detecting electrical characteristics of a remote sample situs according to claim 1, wherein said detected electrical characteristics comprise electrical activity of said remote sample situs.

5. A method of detecting electrical characteristics of a remote sample situs according to claim 4, wherein said electrical characteristics comprise action-potential-related changes in said remote sample situs.

6. A method of detecting electrical characteristics of a remote sample situs according to claim 1, wherein said single optical fiber has a core diameter of between about 50 to 100 $\mu$m.

7. A method of detecting electrical characteristics of a remote sample situs according to claim 6, wherein said single optical fiber includes a cladding layer and an overall diameter of up to about 140 $\mu$m.

8. A method of detecting electrical characteristics of a remote sample situs according to claim 1, further comprising directing said light of a sufficient wavelength to cause fluorescent emission of said dye-treated remote sample situs though a neutral density filter to attenuate said light.

9. A method of detecting electrical characteristics of a remote sample situs according to claim 8, further comprising directing said light of a sufficient wavelength to cause fluorescent emission of said dye-treated remote sample though a short-pass interference filter to remove light of an interfering wavelength.

10. A method of detecting electrical characteristics of a remote sample situs according to claim 9, further comprising directing said received fluorescent emission to said detector utilizing a beam splitter.

11. A method of detecting electrical characteristics of a remote sample situs according to claim 10, further, comprising directing said received fluorescent emission through a long-pass filter to remove any excitation light from said received fluorescent emission.

12. A method of detecting electrical characteristics of a remote sample situs according to claim 1, wherein said dye treated remote sample situs is treated with a voltage-sensitive dye.

13. A method of detecting electrical characteristics of a remote sample situs according to claim 12, wherein said voltage-sensitive dye comprises a styryl voltage-sensitive dye.

14. A method of detecting electrical characteristics of a remote sample situs according to claim 13, wherein the wavelength of said light delivered to said dye-treated remote sample is between about 490 to 550 $\mu$m.

15. A method of detecting electrical characteristics of a remote sample situs according to claim 1, wherein said detector comprises a photomultiplier.

16. A method of detecting electrical characteristics of a remote sample situs according to claim 1, wherein said detector comprises a photodiode.

17. An apparatus for detecting electrical characteristics of a remote sample situs which comprises:
   a light source for generating excitation light having a wavelength of between about 400 to 550 nm;
   means to pass said excitation light through a single optical fiber to a remote sample situs;
   means interposed between said light source and said single optical fiber for attenuating said excitation light;
   means interposed between said attenuating means and said single optical fiber for removing light of an interfering wavelength from said excitation light;
   a fluorescent detector;
   means for directing emitted light from said remote sample situs through said single optical fiber to said fluorescent detector; and
   means positioned between said directing means and said fluorescent detector for removing light of an excitation wavelength from said emitted light.

18. An apparatus for detecting electrical characteristics of a remote sample situs according to claim 17, wherein said single optical fiber has a core diameter of between about 50 to 100 $\mu$m.

19. An apparatus for detecting electrical characteristics of a remote sample situs according to claim 18, wherein said single optical fiber includes a cladding layer and an overall diameter of up to about 140 $\mu$m.

20. An apparatus for detecting electrical characteristics of a remote sample situs according to claim 17, wherein said fluorescent detector comprises a photomultiplier.

* * * * *